United States Patent [19]

Kanter et al.

[11] Patent Number: 4,925,946

[45] Date of Patent: May 15, 1990

[54] PREPARATION OF PYRAZOLO(5,1-B)QUINAZOLONES

[75] Inventors: Hartmut Kanter, Ludwigshafen; Burkhard Ort, Wachenheim, both of Fed. Rep. of Germany

[73] Assignee: BASF Aktiengesellschaft, Ludwigshafen, Fed. Rep. of Germany

[21] Appl. No.: 242,132

[22] Filed: Sep. 9, 1988

[30] Foreign Application Priority Data

Sep. 11, 1987 [DE] Fed. Rep. of Germany ....... 3730535

[51] Int. Cl.$^5$ ............................................. C07D 487/04
[52] U.S. Cl. ................................................... 544/250
[58] Field of Search ......................................... 544/250

[56] References Cited

PUBLICATIONS

K. Menzel et al., *Angew. Chem.* vol. 74, pp. 839–847 (1962).
J. Sircar et al., *Journal of Heterocyclic Chemistry*, vol. 18, 1981, pp. 117–121.
J. Sircar et al., *Journal of Medicinal Chemistry*, vol. 24, 1981, pp. 735–742.

*Primary Examiner*—Richard A. Schwartz
*Attorney, Agent, or Firm*—Oblon, Spivak, McClelland, Maier & Neustadt

[57] ABSTRACT

Pyrazolo[5,1-b]quinazolones are prepared by reacting isatoic anhydrides with 3-methylpyrazol-5-one in water as reaction medium at from 40° to 150° C. under from 1 to 5 bar.

8 Claims, No Drawings

PREPARATION OF PYRAZOLO(5,1-B)QUINAZOLONES

The present invention relates to a novel process for preparing pyrazolo[5,1-b]quinazolones by reacting isatoic anhydrides with 3-methylpyrazol-5-one in water as reaction medium at from 40° to 150° C. under from 1 to 5 bar.

It is known to prepare 2-methylpyrazolo[5,1-b]quinazolone by reacting isatoic anhydride with 3-methylpyrazol-5-one in the melt or in a high-boiling solvent at from 200° to 250° C. (Agnew. Chem. 74 (1962), 839).

J. Heterocycl. Chem. 18 (1981), 117 and J. Med. Chem. 24 (1981), 735 disclose the preparation of further pyrazolo[5,1-b]quinazolones. The starting materials used are likewise isatoic anhydrides and pyrazolones. This reaction takes place in N,N-dimethylformamide as solvent in the presence of sodium hydride as base at from −10° to 0° C.

Neither procedure is easy to carry out on an industrial scale. On the one hand, special measures are required in order to be able to perform the reaction at a very high temperature in a melt or in a high-boiling solvent; on the other hand, the use of sodium hydride as base is not without its problems and necessitates a great deal of attention to safety.

It is an object of the present invention to provide a new process for preparing pyrazolo[5,1-b]quinazolones which starts from industrially readily accessible starting materials and which should give the target products in good yield without recourse to extraordinary technical resources.

We have found that this object is achieved with a process for preparing a pyrazolo[5,1-b]quinazolone of the formula I

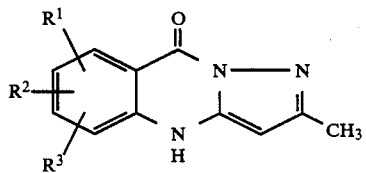

where $R^1$, $R^2$ and $R^3$ are identical or different and each is independently of the others hydrogen, fluorine, chlorine or bromine, by reacting an isatoic anhydride of the formula II

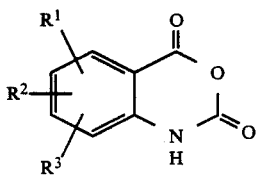

where $R^1$, $R^2$ and $R^3$ are each as defined above, with 3-methylpyrazol-5 one, which comprises performing the reaction in water as reaction medium at from 40° to 150° C. under from 1 to 5 bar.

Isatoic anhydride and 3-methylpyrazol-5-one are in general reacted in a molar ratio of from 1.2:1 to 0.6:1. Both reactants may also be used in this reaction in aqueous paste form.

It is also possible to use 3-methylpyrazol-5-one in the form of its aqueous synthesis solution as in general obtained in the reaction of an ester of acetoacetic acid with hydrazine.

A preferred procedure comprises performing the process according to the invention in the presence of from 5 to 100% by weight, preferably of from 10 to 25% by weight, each based on isatoic anhydride II, of a wetting agent.

Suitable wetting agents for this purpose are surfactants known per se, as described for example in Ullman's Encyklopädie der Technischen Chemie, 4th edition, volume 22, pages 467 to 500. Examples are sodium salts of alkanesulfonates or of fatty acid condensation products.

Preference is also given to a procedure where the starting materials are isatoic anhydrides of the formula IIa

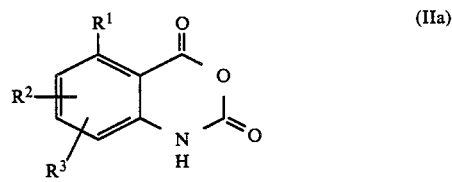

where $R^1$ is fluorine, chlorine or bromine and $R^2$ and $R^3$ are each hydrogen.

Advantageously, the process according to the invention is carried out by introducing water, 3-methylpyrazol-5-one and any wetting agent initially, heating with stirring to from 40° to 100° C., preferably to from 60° to 80° C., and slowly adding the isatoic anhydride. After the evolution of carbon dioxide, which indicates the formation of an open-ring intermediate of the formula III

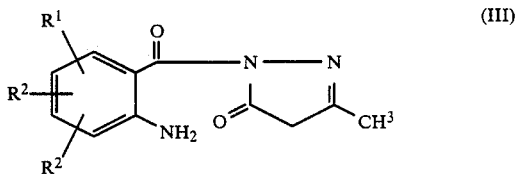

where $R^1$, $R^2$ and $R^3$ are each as defined above, has ceased, the reaction mixture is generally stirred at the abovementioned temperature or preferably at from 60° to 150° C., in particular at from 80° to 130° C., for from 1 to 10 hours.

The reaction is carried out within a pressure range of from 1 to 5 bar, preferably from 1 to 3 bar. The reaction temperature is of course dependent on the reaction pressure. If the process according to the invention is carried out under atmospheric pressure, the upper limit of the temperature range is 100° C. If the process is carried out at a higher pressure, the upper temperature limit is higher.

After the reaction has ended, the resulting pyrazolo[5,1-b]quinazolone of the formula I is separated off, washed with water and dried.

Using the process according to the invention, which may be carried out not only continuously but also batchwise, pyrazolo[5,1-b]quinazolones can be obtained without recourse to extraordinary technical resources and, surprisingly, without using an organic solvent.

A further advantage of the novel process is that any unconverted starting material, intermediate III and anthranilic acids formed by back cleavage from intermediate III are easy to separate from the target product. This is because the compounds mentioned dissolved in warm water at a pH of from 6.5 to 8.5, preferably at from 7.0 to 7.5. It is thus in general sufficient to bring the reaction mixture into the desired pH range by adding a little base (for example sodium hydroxide or potassium hydroxide solution) and filter off the pyrazolo[5,1-b]quinazolone.

Pyrazolo[5,1-b]quinazolones, which are obtained in good yields, are useful intermediates for the synthesis of dyes and pigments.

The Examples which follow serve to illustrate the invention in more detail.

EXAMPLE 1

300 g of 3-methylpyrazol-5-one and 50 g of a wetting agent based on the sodium salt of a fatty acid condensation product were introduced initially in 6,000 ml of water and heated with stirring to 75° C. 500 g of isatoic anhydride were then added in the course of 2 hours and stirred in over 10 hours. The reaction mixture was then brought to pH 8.5 with 10% strength by weight sodium hydroxide solution, subsequently stirred for 1 hour and filtered with suction, and the filter residue was washed with warm water and dried to leave 400 g of a colorless powder of the formula

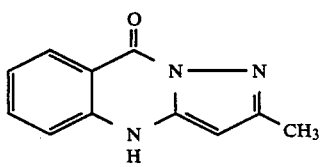

EXAMPLE 2

100 g of 3-methylpyrazol-5-one were initially introduced in 600 ml of water and heated to 70° C., and 200 g of 6-chloroisatoic anhydride were slowly added. The reaction mixture was stirred for 1 hour, heated to 90° C. and stirred for a further 2 hours. It was subsequently brought to pH 8 with sodium carbonate, stirred for 1 hour and filtered with suction, and the filter residue was washed with warm water and dried to leave 200 g of a colorless powder of the formula

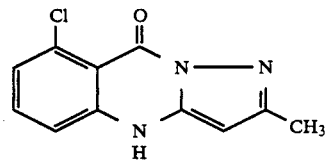

EXAMPLE 3

40 g of 3-methylpyrazol-5-one and 10 g of a wetting agent based on the sodium salt of a fatty acid condensation product were introduced initially in 650 ml of water and heated to 70° C., and 110 g of 3,5,6-trichloroisatoic anhydride were slowly added. The reaction mixture was stirred for 3 hours, heated to 130° C. and stirred for a further 5 hours. After cooling to 80° C. it was brought to pH 8.5 with 5% strength by weight sodium hydroxide solution, stirred for 1 hour and filtered with suction, and the filter residue was washed with warm water and dried to leave 70 g of a light-colored powder of the formula

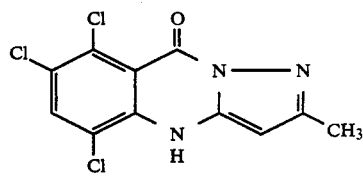

The compounds listed in the table below with the reaction temperatures and the yield were obtained in a similar manner.

| Example No. | Formula | Reaction temperature [°C.] | Yield [%] |
| --- | --- | --- | --- |
| 4 | ![] | 70/130 | 65 |
| 5 | ![] | 70/90 | 87 |
| 6 | ![] | 70/90 | 83 |

| Example No. | Formula | Reaction temperature [°C.] | Yield [%] |
|---|---|---|---|
| 7 | 5-Br, 3-methylpyrazole anthranilamide derivative | 80/120 | 53 |
| 8 | 4-Br isomer | 80/120 | 67 |
| 9 | 4-Cl isomer | 80/120 | 73 |
| 10 | 3,5-diBr isomer | 80/130 | 63 |
| 11 | 3,5-diCl isomer | 80/130 | 61 |
| 12 | 3,4,5-triCl isomer | 80/120 | 57 |
| 13 | 3,5-diBr-4-Cl isomer | 80/110 | 73 |

EXAMPLE 14

104 g of methyl acetoacetate were initially introduced in 40 ml of water. 48 g of hydrazine hydrate were added at from 35° to 40° C. in the course of 1 hour. This was followed by 2 hours of stirring at from 35° to 40° C., addition of a further 7 g of methyl acetoacetate and further stirring at 55° C. for 2 hours. The reaction mixture was brought to pH 7 with 10% strength by weight sodium hydroxide solution. It was then diluted with 2 l of water and heated to 80° C., and 198 g of 6-chloroisatoic anhydride were added in the course of 30 minutes. The reaction mixture was then stirred at 80° C. for 5 hours and at 95° C. for 1 hour and brought to pH 8 with 10% strength by weight sodium hydroxide solution. The reaction product was filtered off with suction, washed with warm water and dried to leave 190 g of a colorless powder of the formula

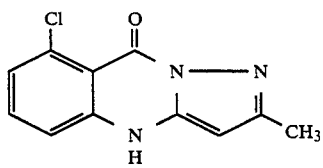

We claim:

1. A process for preparing a pyrazolo[5,1-b]quinazolone of the formula I

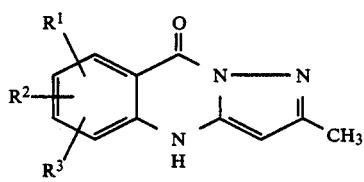

where $R^1$, $R^2$ and $R^3$ are identical or different and each is independently of the others hydrogen, fluorine, chlorine or bromine, by reacting an isatoic anhydride of the formula II

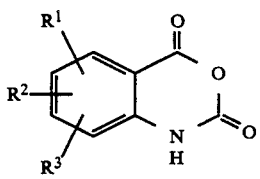

where $R^1$, $R^2$ and $R^3$ are each as defined above, with 3-methylpyrazol-5-one, which comprises performing the reaction in water as a reaction medium at from 40° to 150° C. under a pressure of from 1 to 5 bar.

2. The process as claimed in claim 1, wherein the reaction is carried out in the presence of a wetting agent.

3. The process as claimed in claim 1, wherein the reaction is carried out with an isatoic anhydride of the formula IIa

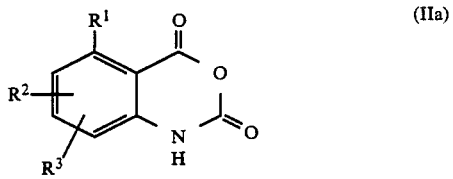

where $R^1$ is fluorine, chlorine or bromine and $R^2$ and $R^3$ are each hydrogen.

4. The process as claimed in claim 1, wherein said isatoic anhydride and 3-methylpyrazol-5-one are reacted in a molar ratio of from 1.2:1 to 0.6:1.

5. The process as claimed in claim 2, wherein said reaction is conducted in the presence of from 5 to 100% by weight, based on the amount of isatoic anhydride used, of a wetting agent.

6. The process as claimed in claim 1, wherein said 3-methyl-pyrazol-5-one is heated with stirring to 40° to 100° C., while slowly adding said isatoic anhydride, and, after the evolution of carbon dioxide, conducting said reaction at from 60° to 150° C.

7. The process as claimed in claim 5, wherein said wetting agent is used in the amount of from 10 to 25% by weight based on the amount of isatoric anhydride.

8. The process as claimed in claim 1, wherein a pressure of from 1 to 3 bar is used for said reaction.

* * * * *